(12) United States Patent
Gogly et al.

(10) Patent No.: US 7,951,593 B2
(45) Date of Patent: May 31, 2011

(54) CULTURE MEDIUM FOR GINGIVAL FIBROBLASTS

(75) Inventors: Bruno Gogly, Hondevilliers (FR); Bernard Coulomb, Igny (FR); Antoine Lafont, Paris (FR)

(73) Assignee: Universite Rene Descartes-Paris V, Paris (FR)

( * ) Notice: Subject to any disclaimer, the term of this patent is extended or adjusted under 35 U.S.C. 154(b) by 92 days.

(21) Appl. No.: 12/051,559

(22) Filed: Mar. 19, 2008

(65) Prior Publication Data

US 2009/0061512 A1  Mar. 5, 2009

Related U.S. Application Data

(60) Provisional application No. 60/895,809, filed on Mar. 20, 2007.

(51) Int. Cl.
*C12N 5/00* (2006.01)
*C12N 5/02* (2006.01)

(52) U.S. Cl. ........ 435/405; 435/404; 435/325; 435/357; 435/366

(58) Field of Classification Search .................. None
See application file for complete search history.

(56) References Cited

U.S. PATENT DOCUMENTS

| | | |
|---|---|---|
| 4,927,762 A | 5/1990 | Darfler |
| 6,617,159 B1 * | 9/2003 | Cancedda et al. ............ 435/325 |
| 2002/0076747 A1 | 6/2002 | Price et al. |
| 2003/0190748 A1 | 10/2003 | Thomson |
| 2005/0233446 A1 | 10/2005 | Parsons |
| 2006/0073587 A1 | 4/2006 | Stice et al. |
| 2008/0025954 A1 | 1/2008 | Lafont et al. |

FOREIGN PATENT DOCUMENTS

| | | |
|---|---|---|
| EP | 0 350 887 | 1/1990 |
| WO | WO-2005/105984 | 11/2005 |

OTHER PUBLICATIONS

Marcopoulou et al., J Int Acad Periodontol. Jul. 2003;5(3):63-70; Abstract only.*
Soory et al, "Anabolic potential of fibroblasts from chronically inflamed gingivae grown in a hyperglycemic cluture medium in the presence or absence of insulin and nicotine.", Dec. 2003, pp. 1771-1777, vol. 74, No. 12, Journal of Periodontology.
Ta et al, "Heparan sulfate interacting protein (HIP/L29) negatively regulates growth responses to basic fibroblast growth factor in gingival fibroblasts.", Apr. 2002, pp. 247-252, vol. 81, No. 4., Journal of Dental Research.
Doucet et al, "Platelet lysates promote mesenchymal stem cell expansion: A safety substitute for animal serum in cell-based therapy applications", Nov. 1, 2005, pp. 228-236, vol. 205, No. 2., Journal of Cellular Physiology, Liss, New York, NY, USA.
Liselott et al, "Platelet lysate: a replacement for fetal bovine serum in animal cell culture?", Jun. 1, 2003, pp. 67-74, vol. 42, No. 2, Cytotechnology, Kluwer Academic Publishers, DO.

* cited by examiner

*Primary Examiner* — David S Romeo
*Assistant Examiner* — Daniel C Gamett
(74) *Attorney, Agent, or Firm* — Stites & Harbison PLLC; B. Aaron Schulman; Stephen J. Weyer

(57) ABSTRACT

The present invention relates to a gingival fibroblast culture medium free of animal serum, comprising an animal cell culture medium, free of animal serum, to which is added:
from 0.1 ng/ml to 100 ng/ml bFGF, and/or
from 1 µg/ml to 50 µg/ml insulin.

6 Claims, 4 Drawing Sheets

SEQUENCE LISTING

```
<160> NUMBER OF SEQ ID NOS: 1

<210> SEQ ID NO 1
<211> LENGTH: 155
<212> TYPE: PRT
<213> ORGANISM: Homo sapiens

<400> SEQUENCE: 1

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly Arg
        35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

CULTURE MEDIUM FOR GINGIVAL FIBROBLASTS

This application claims benefit of U.S. Provisional Application No. 60/895,809, filed Mar. 20, 2007 (which is hereby incorporated by reference).

FIELD OF THE INVENTION

The present invention relates to a culture medium, free of animal serum, specifically adapted for the culture of gingival fibroblasts.

BACKGROUND OF THE INVENTION

Gingival fibroblasts are mesenchymal cells which are capable of migrating, adhering and proliferating within the soft connective tissues of the gum, thereby maintaining the integrity of the gingival tissue, which is exposed to numerous aggressions, such as mechanical stresses, bacterial infections, or pH and temperature variations. Gingival fibroblasts are in particular described in Gogly et al., (1997) *Clin. Oral Invest.* 1:147-152; Gogly et al. (1998) *Biochem. Pharmacol.* 56:1447-1454; and Ejeil et al. (2003) *J. Periodontol.* 74:188-195.

Depending on environmental conditions, gingival fibroblasts are capable to modulate their phenotype, and to respond by proliferating, migrating, synthesising matrix components or matrix-related enzymes. Gingival fibroblasts notably synthesise collagens (e.g. types I, III, V, VI, VII, XII) elastic fibers (oxytalan, elaunin and elastin), proteoglycans and glycosaminoglycans (e.g. decorin, biglycan), and glycoproteins (e.g. fibronectin, tenascin). Simultaneously, gingival fibroblasts synthesise enzymes that are able to degrade the macromolecular compounds (matrix metalloproteinases; MMPs), but also enzymes inhibiting active forms of MMPs (Inhibitors of metalloproteinases; TIMPs). Gingival fibroblasts are thus important actors of extracellular matrix remodelling.

Gingival fibroblasts have been shown to treat arterial-remodelling pathologies (WO 2006/013261) and more recently to promote and to accelerate skin wound healing.

Thus, the potential of gingival fibroblasts in cell-therapy appears promising and highlights the need for culture methods liable to yield large quantities of these cells.

Current culture media for gingival fibroblasts are well defined (Gogly et al. op. cit.). These culture media all make use of foetal calf serum (FCS). Indeed, it could be shown that gingival fibroblasts had very precise requirements in term of FCS concentration in the culture medium, since less than 10% FCS not only causes a decreased growth of gingival fibroblasts but also causes gingival fibroblasts to present a high lactate deshydrogenase (LDH) activity, which is indicative of cellular suffering (see FIGS. 1 and 2).

However, FCS, and animal sera in general, are unwanted in culture media used to cultivate and/or differentiate cells for human cell-therapy. Indeed, the composition of animal sera is usually variable and badly characterized (Morris & Warburton (1994) *"Serum-screening and selection" in "Cell & Tissue Culture: Laboratory Procedures"* (Doyle, Griffiths and Newell, eds) pp. 2B:101-105, Wiley). Moreover, these sera are liable to be contaminated by micro-organisms or prion and therefore are liable to be health-threatening to the patient for whom the cultivated cells are intended (Wessman & Levings (1999) *Dev. Biol. Stand.* 99:3-8).

Serum-free culture media for animal cells are known in the art and are commercially available. Thus, one may cite for instance the serum replacement formulation KNOCKOUT™ SR from GIBCO™ which is added to Dulbecco's Modified Eagle's Medium (DMEM), instead of FCS, to yield a serum-free culture medium. However, it has never been asserted that such a medium was liable to provide for adequate serum-free growth conditions of gingival fibroblasts, which, as recalled above, are known to have very specific requirements in term of FCS concentrations. Besides, these media have not been specifically designed to provide for gingival fibroblast culture conditions suited for therapeutic use, that is, culture conditions liable to rapidly yield large quantities of functional gingival fibroblasts.

Thus, it is an object of the present invention to improve existing serum-free culture media for animal or human cells in order to provide for optimal growth of gingival fibroblasts.

SUMMARY OF THE INVENTION

The present invention arises from the finding, by the inventor, that adding basic Fibroblast Growth Factor (bFGF) at a concentration of from 0.1 ng/ml to 100 ng/ml, in particular at about 1 ng/ml, and/or insulin at a concentration of from 1 µg/ml to 50 µg/ml, in particular at about 5 µg/ml, to a culture medium for animal or human cells free of animal serum, improved the growth of gingival fibroblasts cultured therein with respect to the culture medium for animal or human cells free of animal serum which would not be added with bFGF and/or insulin at these concentrations.

As such, the present invention relates to a gingival fibroblast culture medium free of animal serum, comprising a culture medium for animal or human cells, free of animal serum, to which is added:
 (i) human serum, and/or
 (ii) from 0.1 ng/ml to 100 ng/ml, in particular about 1 ng/ml, bFGF and/or from 1 µg/ml to 50 µg/ml in particular about 5 µg/ml, insulin.

The present invention also relates to the use of a culture medium for animal or human cells, free of animal serum, to which is added:
 (i) human serum, and/or
 (ii) from 0.1 ng/ml to 100 ng/ml, in particular about 1 ng/ml, bFGF and/or from 1 µg/ml to 50 µg/ml, in particular about 5 µg/ml, insulin,
for the culture of gingival fibroblast.

The present invention also relates to a method for the culture of gingival fibroblasts which comprises growing cells in a culture medium for animal or human cells, free of animal serum, to which is added:
 (i) human serum, and/or
 (ii) from 0.1 ng/ml to 100 ng/ml, in particular about 1 ng/ml, bFGF and/or from 1 µg/ml to 50 µg/ml, in particular about 5 µg/ml, insulin.

In an embodiment of the above defined gingival fibroblast culture medium, use or method, the culture medium for animal or human cells, free of animal serum, is further added with platelet lysate.

The present invention also relates to a kit for cultivating gingival fibroblasts, comprising:
 a gingival fibroblast culture medium free of animal serum as defined above, and
 platelet lysate.

Advantageously, gingival fibroblast culture medium, free of animal serum, according to the invention provides for growth of gingival fibroblasts, in particular human gingival fibroblasts, equivalent to the growth which can be attained in a similar medium containing FCS, in particular 10% FCS which is recognized as the reference FCS concentration for growing gingival fibroblasts.

DETAILED DESCRIPTION OF THE INVENTION

Figure 1:
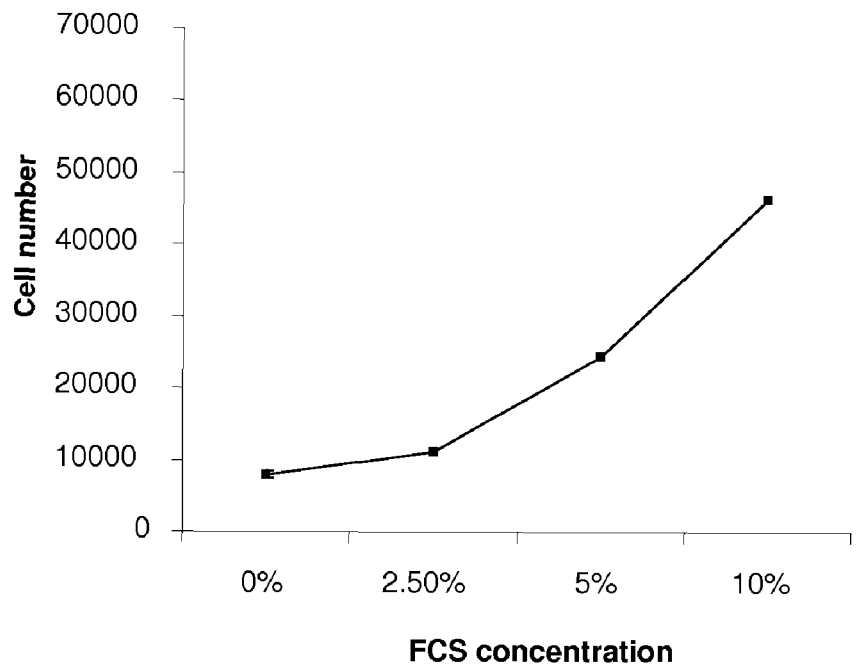
FIG. 1 represents the growth of gingival fibroblasts (vertical axis, cell number) cultivated in culture media comprising 0%, 2.5%, 5% or 10% FCS (horizontal axis).
Figure 2:
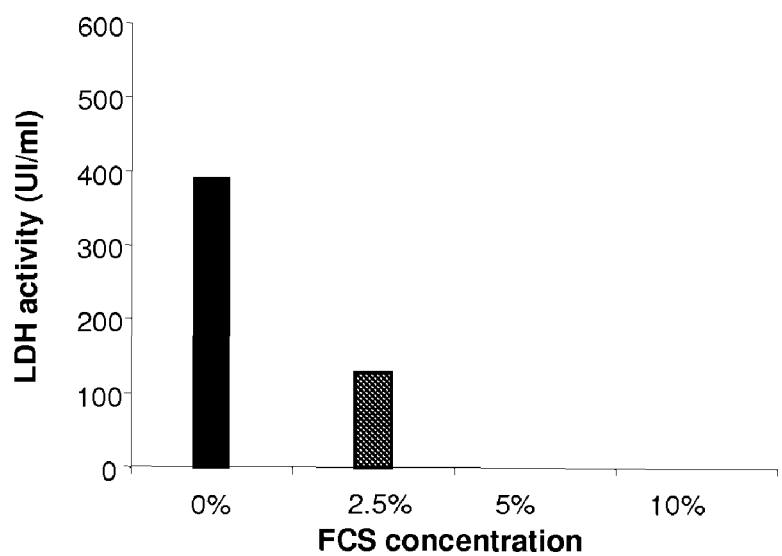
FIG. 2 represents the lactate deshydrogenase (LDH) activity (vertical axis, UI/ml) of gingival fibroblast culture supernatant as a function of the FCS content of the culture medium (horizontal axis).

As intended herein "gingival fibroblasts" relate to mesenchymal cells of the gum, which are capable of migrating, adhering and proliferating within the soft connective tissues of the gum. Gingival fibroblasts and methods to obtain them are notably described in Gogly et al., (1997) *Clin. Oral Invest.* 1:147-152; Gogly et al. (1998) *Biochem. Pharmacol.* 56:1447-1454; and Ejeil et al. (2003) *J. Periodontol.* 74:188-195. Preferably, gingival fibroblasts according to the invention are human gingival fibroblasts.

Basic Fibroblast Growth Factor (bFGF) is well known to one of skill in the art. Preferably, bFGF relates to human bFGF, more preferably to recombinant human bFGF, and even more preferably to recombinant human bFGF represented by SEQ ID NO: 1 and produced in *Escherichia coli*.

Insulin is well known to one of skill in the art. Preferably, insulin relates to human insulin, more preferably to recombinant human insulin, and even more preferably to recombinant human insulin produced in *Escherichia coli*. It is preferred that insulin is present in the Zn-insulin form, i.e. insulin molecules and zinc ions liganded together.

The expression "culture medium for animal or human cells, free of animal serum" relates to culture media well known to one of skill in the art. It notably relates to any culture medium, free of animal serum, liable to sustain the growth of animal or human cells. Preferably, a "culture medium for animal or human cells, free of animal serum" according to the invention is liable to sustain the growth of gingival fibroblasts according to the invention, but only to a level which is significantly lower to the level which could be reached under the same culture conditions with a culture medium suitable for gingival fibroblast growth which comprises a growth-effective amount of FCS. In particular, a "culture medium for animal or human cells, free of animal serum" can be obtained by mixing a basal culture medium with a serum-free culture supplement intended for substituting for animal serum.

Preferably, the basal culture medium is Dulbecco's Modified Eagle's Medium (DMEM). Such a medium is well known to one of skill in the art and is notably described in Dulbecco and Freeman (1959) *Virology* 8:396.

Most preferably, DMEM has the following constitution:

| Components | MW | Concentration (mg/L) | Molarity (mM) |
|---|---|---|---|
| Amino acids | | | |
| Glycine | 75 | 30 | 0.400 |
| L-Arginine hydrochloride | 211 | 84 | 0.398 |
| L-Cystine 2HCl | 313 | 63 | 0.201 |
| L-Glutamine | 146 | 580 | 3.97 |
| L-Histidine hydrochloride-H$_2$O | 210 | 42 | 0.200 |
| L-Isoleucine | 131 | 105 | 0.802 |
| L-Leucine | 131 | 105 | 0.802 |
| L-Lysine hydrochloride | 183 | 146 | 0.798 |
| L-Methionine | 149 | 30 | 0.201 |
| L-Phenylalanine | 165 | 66 | 0.400 |
| L-Serine | 105 | 42 | 0.400 |
| L-Threonine | 119 | 95 | 0.798 |
| L-Tryptophan | 204 | 16 | 0.0784 |
| L-Tyrosine | 181 | 72 | 0.398 |
| L-Valine | 117 | 94 | 0.803 |
| Vitamins | | | |
| Choline chloride | 140 | 4 | 0.0286 |
| D-Calcium pantothenate | 477 | 4 | 0.00839 |
| Folic Acid | 441 | 4 | 0.00907 |
| i-Inositol | 180 | 7.2 | 0.0400 |
| Niacinamide | 122 | 4 | 0.0328 |
| Pyridoxine hydrochloride | 204 | 4 | 0.0196 |
| Riboflavin | 376 | 0.4 | 0.00106 |
| Thiamine hydrochloride | 337 | 4 | 0.0119 |
| Inorganic salts | | | |
| Calcium Chloride (CaCl$_2$—2H$_2$O) | 147 | 264 | 1.80 |
| Ferric Nitrate (Fe(NO$_3$)$_3$—9H$_2$O) | 404 | 0.1 | 0.000248 |
| Magnesium Sulfate (MgSO$_4$—7H$_2$O) | 246 | 200 | 0.813 |
| Potassium Chloride (KCl) | 75 | 400 | 5.33 |
| Sodium Bicarbonate (NaHCO$_3$) | 84 | 3700 | 44.05 |
| Sodium Chloride (NaCl) | 58 | 6400 | 110.34 |
| Sodium Phosphate monobasic (NaH$_2$PO$_4$—2H$_2$O) | 154 | 141 | 0.916 |
| Other components | | | |
| D-Glucose (Dextrose) | 180 | 4500 | 25.00 |
| Phenol Red | 376.4 | 15 | 0.0399 |
| Sodium Pyruvate | 110 | 110 | 1.000 |

As intended herein a "serum-free supplement" preferably relates to a medium containing serum albumin, in particular bovine serum albumin, and one or more ingredients selected from the group consisting of one or more amino acids, one or more vitamins, transferrin, in particular in its iron saturated form, one or more antioxidants (e.g. glutathione and L-ascorbic acid-2-phosphate), and insulin.

Such a serum-free supplement is described international application WO 98/30679 which is incorporated herein by reference.

In a preferred embodiment the serum-free supplement is KNOCKOUT™ SR (INVITROGEN, ref. 10828-028). Preferably, the culture medium for animal or human cells, free of animal serum, is obtained by mixing from 7 to 9 volumes of DMEM as defined above to 1 to 3 volumes KNOCKOUT™ SR serum-free supplement. More preferably, the culture medium for animal or human cells, free of animal serum, is obtained by mixing 8 volumes of DMEM as defined above to 2 volumes KNOCKOUT™ SR serum-free supplement or 9 volumes of DMEM as defined above to 1 volume KNOCKOUT™ SR serum-free supplement.

In another preferred embodiment the serum-free supplement is such that it presents the following concentrations of its components upon addition to the basal culture medium:

| Components | Concentration (mg/L) |
|---|---|
| Concentration of non trace components | |
| Glycine | 53 |
| L-Histidine | 183 |
| L-Isoleucine | 615 |
| L-Methionine | 44 |
| L-Phenylalanine | 336 |
| L-Proline | 600 |
| L-Hydroxyproline | 15 |
| L-Serine | 162 |
| L-Threonine | 425 |
| L-Tryptophan | 82 |
| L-Tyrosine | 84 |
| L-Valine | 454 |
| Thiamine | 9 |
| Reduced glutathione | 1.5 |
| Ascorbic acid-2-PO$_4$ (Mg salt) | 50 |
| Transferrin (ironsaturated) | 8 |
| Insulin | 10 |
| Sodium selenite | 0.00001 |
| Bovine serum albumin | 12,500 |
| Concentration of trace components | |
| Ag$^+$ | 0.00009 |
| Al$^{3+}$ | 0.0001 |
| Ba$^{2+}$ | 0.001 |
| Cd$^{2+}$ | 0.005 |
| Co$^{2+}$ | 0.0005 |
| Cr$^{3+}$ | 0.00004 |
| Ge$^{4+}$ | 0.0005 |
| Se$^{4+}$ | 0.007 |
| Br$^-$ | 0.00006 |
| I$^-$ | 0.0001 |
| Mn$^{2+}$ | 0.00006 |
| F$^-$ | 0.002 |
| Si$^{4+}$ | 0.02 |
| V$^{5+}$ | 0.0004 |
| Mo$^{6+}$ | 0.0007 |
| Ni$^{2+}$ | 0.00003 |
| Rb$^+$ | 0.0008 |
| Sn$^{2+}$ | 0.00003 |
| Zr$^{4+}$ | 0.0001 |

It is preferred that the serum albumin used in the serum-free supplement is bovine serum albumin (BSA), either recombinant or extracted for bovine tissues. Most preferably, serum albumin relates to lipid-rich serum albumin extracts from bovine tissues, such as Albumax® I (Invitrogen).

Most preferably, the culture medium for animal or human cells, free of animal serum, further comprises one or more ingredients selected from the group constituted of non-essential amino acids, in particular 1% v/v of a solution comprising Glycine 10 mM, L-Alanine 10 mM, L-Asparagine 10 mM, L-Aspartic acid 10 mM, L-Glutamic Acid 10 mM, L-Proline 10 mM, L-Serine 10 mM; β-mercaptoethanol, in particular at 1 mM; antibiotics; and fungicides.

Preferably, upon addition of bFGF and/or insulin to the culture medium for animal or human cells, free of animal serum, as defined above, the resulting medium, in particular the gingival fibroblast culture medium as defined above, comprises bFGF at a concentration of from 0.1 ng/ml to 100 ng/ml, in particular about 1 ng/ml, and/or insulin at a concentration of from 11 µg/ml to 60 µg/ml, in particular about 15 µg/ml. More preferably, the resulting medium comprises bFGF at a concentration of from 0.1 ng/ml to 100 ng/ml, in particular about 1 ng/ml, and insulin at a concentration of from 11 µg/ml to 60 µg/ml, in particular about 15 µg/ml. Most preferably, the resulting medium comprises bFGF at a concentration of about 1 ng/ml and insulin at a concentration of about 15 µg/ml.

As intended herein "platelet lysate" preferably relates to a lysate of human platelets. Preferably the platelets are in the form of a platelet concentrate. Platelet lysates and methods of preparation thereof are notably described in Doucet et al. (2005) *J. Cellular Physiol.* 205:228-236.

Preferably, an effective quantity of platelet lysate is added, that is a quantity such that the gingival fibroblast culture medium added with platelet lysate offers improved growth conditions for gingival fibroblast with respect to the same gingival fibroblast culture medium deprived of platelet lysate.

By way of example, a platelet lysate can be prepared by adding 4 µl heparin at 25,000 IU/ml to 47.5 ml of basal culture medium or a serum-free supplement, vortexing, adding 2.5 ml of a human platelet concentrate comprising at least 2.109 platelets, and vortexing to lyse the platelets.

EXAMPLES

Example 1

Definition of the Composition of a Serum-Free Culture Medium for Gingival Fibroblasts 1. The following culture media are compared:
Gingival fibroblasts serum-containing culture medium (FCS):
DMEM 90% (INVITROGEN, ref. 41966-029);
FCS 10% (INVITROGEN, ref 16000-044)
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 µg/ml, and amphotericin B 250 ng/ml) (INVITROGEN, ref. 15240-062)
bFGF-supplemented gingival fibroblast serum-free culture medium (KOS/bFG F):
DMEM 80% (INVITROGEN, ref. 41966-029);
KNOCKOUT™ SR 20% (INVITROGEN, ref. 10828-028) optionally+platelet lysate;
Human recombinant bFGF 0-100 nci/ml (INVITROGEN, ref. 13256-029);
Non-essential amino acids 1% (INVITROGEN, ref. 11140-035);

β-mercaptoethanol 0.1 mM (INVITROGEN, ref. 31350-010).
Antibiotic-Antimicotic 1×(penicillin 100 units/ml, streptomycin 100 μg/ml, and amphotericin B 250 ng/ml) (INVITROGEN, ref. 15240-062).

Insulin-supplemented gingival fibroblast serum-free culture medium (KOS/I):

DMEM 80% (INVITROGEN, ref. 41966-029);
KNOCKOUT™ SR 20% (INVITROGEN, ref. 10828-028) optionally+platelet lysate;
Human recombinant Zn Insulin 0-50 μg/ml (MW 5734) (INVITROGEN, ref. R33750)
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 μg/ml, and amphotericin B 250 ng/ml) (INVITROGEN, ref. 15240-062).

The platelet lysate is prepared by adding 4 μl heparin at 25,000 IU/ml to 47.5 ml of a 100% KNOCKOUT™ SR solution, vortexing, adding 2.5 ml of a human platelet concentrate, and vortexing to lyse the platelets. 2×50 ml of the obtained solution are then added to 400 ml of DMEM.

Five Human Gingival Fibroblast (hGF) cultures were obtained from gingival explants of healthy patients (two females and three males from 19 to 31 years old) with no history of periodontitis between January and April 2007. All patients gave their informed consent according to the Helsinki Declaration (1975) and denied having recently taken drugs that could affect connective tissue metabolism. Tissue samples were divided into two parts: one for histologic analysis and the other for cell culture. Serial tissue sections were stained with hematoxylin and eosin for assessing the tissue quality and the absence of inflammatory infiltrates in the gingiva. Only the histological healthy tissue was used for cell culture. Primary explants cultures were established in 25 cm$^2$ culture flasks during 3 weeks with 20% FCS or serum-free medium according to the invention. Monolayer cultures were maintained in 5% $CO_2$, and the cell culture medium was changed every 48 hours. After the first passage, the cells were routinely maintained in 10% FCS or serum-free medium according to the invention during a week. hGFs were used from passages 3. All reported experiments were done with five different strains of gingival fibroblasts. Very similar data were obtained for the five different strains used in each case; representative data of triplicate experiments are presented in each figure.

10,000 human gingival fibroblasts are seeded per 500 μl well of microculture plates, each well further receiving either one of the FCS, KOS/bFGF and KOS/I culture media. The fibroblasts are then cultured over a 6-days period. At day 6 the media from a set of wells are gently taken and cells adhering to the walls of the wells are detached by trypsinization and counted.

Figure 3:
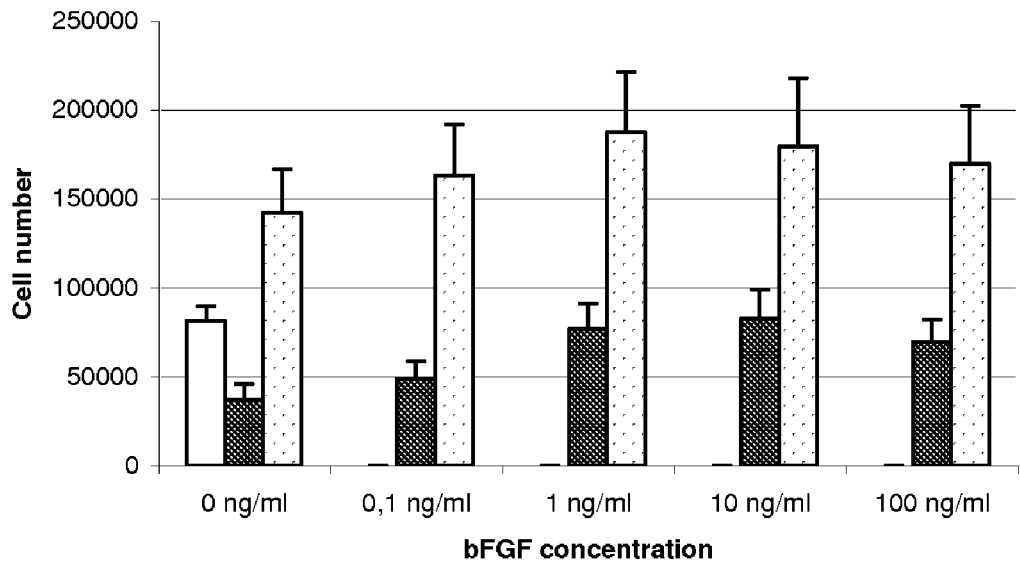
FIG. 3 represents gingival fibroblast proliferation at day 6 of culture (vertical axis, cell number) in culture media free of animal serum supplemented with 0.1, 1, 10 or 100 ng/ml of bFGF (horizontal axis) with (dotted bar) or without platelet lysate (black bar), as compared to the proliferation in a culture medium containing 10% FCS.
Figure 4:
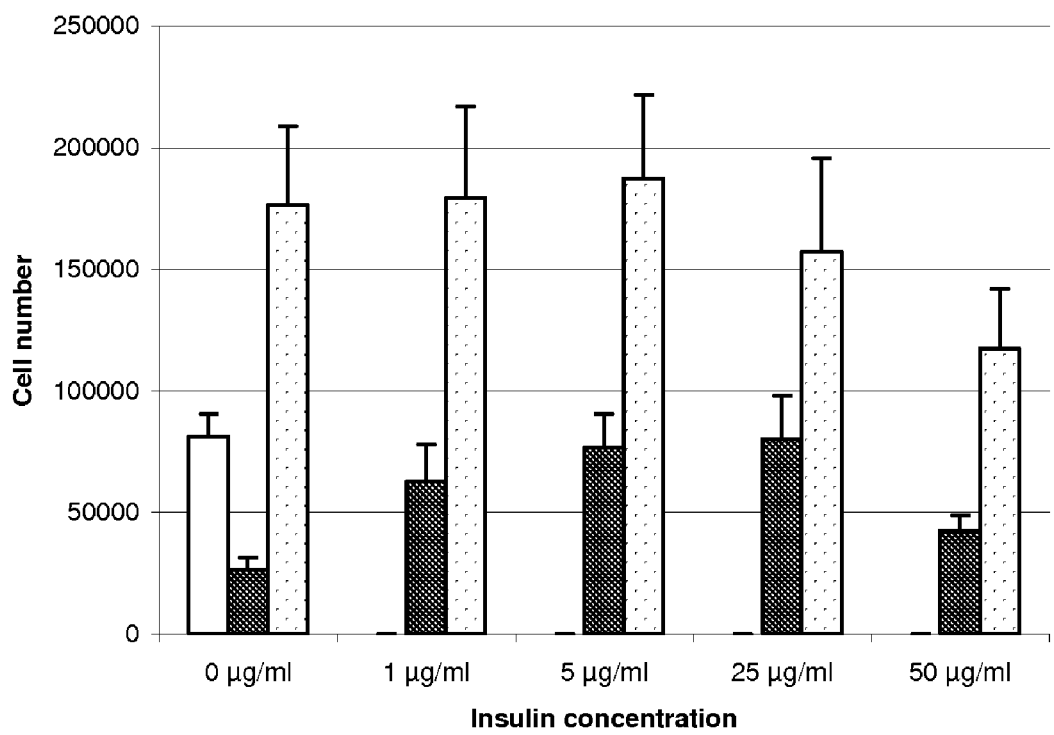
FIG. 4 represents gingival fibroblast proliferation at day 6 of culture (vertical axis, cell number) in culture media free of animal serum supplemented with 1, 5, 25 or 5 µg/ml of insulin (horizontal axis) with (dotted bar) or without platelet lysate (black bar), as compared to the proliferation in a culture medium containing 10% FCS.

The results are presented in FIG. 3 for KOS/bFGF and in FIG. 4 for KOS/I. At 1 ng/ml bFGF, proliferation of gingival fibroblasts in the KOS/bFGF medium is identical to that in FCS and the proliferation in the KOS/bFGF medium supplemented with platelet lysate is at its maximum. At 5 μg/ml Zn Insulin proliferation of gingival fibroblasts in the KOS/I medium is identical to that in FCS and the proliferation in the KOS/I medium supplemented with platelet lysate is at its maximum.

2. These results are confirmed with the following media:
KNOCKOUT™ SR-variable gingival fibroblast serum-free culture medium DMEM 100%-70% (INVITROGEN, ref. 41966-029);
KNOCKOUT™ SR 0%-30% (INVITROGEN, ref. 10828-028);
Human recombinant Zn Insulin 5 μg/ml (MW 5734) (INVITROGEN, ref. R33750)
Human recombinant bFGF 1 ng/ml (INVITROGEN, ref. 13256-029);
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 μg/ml, and amphotericin B 250 ng/ml) (INVITROGEN, ref. 15240-062).

bFGF-variable gingival fibroblast serum-free culture medium (KOS/bFGF):

DMEM 90% (INVITROGEN, ref. 41966-029);
KNOCKOUT™ SR 10% (INVITROGEN, ref. 10828-028) optionally+platelet lysate;
Human recombinant Zn Insulin 5 μg/ml (MW 5734) (INVITROGEN, ref. R33750)
Human recombinant bFGF 0-100 nci/ml (INVITROGEN, ref. 13256-029);
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 μg/ml, and amphotericin B 250 ng/ml) (INVITROGEN, ref. 15240-062).

Insulin-variable gingival fibroblast serum-free culture medium (KOS/I):

DMEM 90% (INVITROGEN, ref. 41966-029);
KNOCKOUT™ SR 10% (INVITROGEN, ref. 10828-028) optionally+platelet lysate;
Human recombinant Zn Insulin 0-50 μg/ml (MW 5734) (INVITROGEN, ref. R33750)
Human recombinant bFGF 1 ng/ml (INVITROGEN, ref. 13256-029);
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 μg/ml, and amphotericin B 250 ng/ml) (INVITROGEN, ref. 15240-062).

The same culture experiments as above are performed. At day 6, counts are done by flow cytometry, and a Trypan-blue stain is shown on one well for each condition permitting a cell quality control.

Cell proliferation increases non-linearly with KNOCKOUT™ SR concentration. The first 5% (from 0% to 5%) lead to increase cells count of a 1.4 factor, and the following (from 5% to 10%) lead to an increase of a 1.8 factor. The first 10% (from 0% to 10%) leads to an increase in cell count of a factor 2.5, while the following 10% (from 10% to 20%) lead to a 1.3 factor increase, and the last 10% (from 20% to 30%) to a 1.15 factor increase. 10% KNOCKOUT™ SR appears to have similar effects on proliferation than the FCS medium at day 6 (respectively $7.5.10^4$ and $7.3.10^4$ cells).

When bFGF is varied, cell proliferation is maximal for bFGF concentration of 1 and 10 ng/ml, which corresponds to the FCS medium reference level. From 0 ng/ml to 0.1 ng/ml, proliferation increases less (1.32 and 2.08 factors respectively). The highest concentration induces a proliferation decrease (factor 0.8 from 10 to 100 ng/ml). When platelet lysate is added, cell proliferation reaches a maximum with 1 ng/ml, and slightly decreases with superior concentration. From 0 ng/ml to 1 ng/ml, proliferation with and without platelet lysate is similar (1.32 factor increase).

When insulin is varied, cellular counting shows higher values with 5 and 25 µg/ml insulin. Proliferation rates in the presence of platelet lysate slightly increase from 0 to 5 µg/ml, before decreasing.

Example 2

Adhesion Test

The following culture media are used:
Gingival fibroblasts serum-containing culture medium (FCS):
DMEM 90% (INVITROGEN, ref. 41966-029);
FCS 10% (INVITROGEN, ref 16000-044)
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 µg/ml, and amphotericin B 250 ng/ml) (INVITROGEN, ref. 15240-062)
Gingival fibroblast serum-free culture medium (KOS):
DMEM 80% (INVITROGEN, ref. 41966-029);
KNOCKOUT™ SR 20% (INVITROGEN, ref. 10828-028);
Human recombinant bFGF 1 ng/ml (INVITROGEN, ref. 13256-029);
Human recombinant Zn Insulin 5 µg/ml (MW 5734) (INVITROGEN, ref. R33750)
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 µg/ml, and amphotericin B 250 ng/ml) (INVITROGEN, ref. 15240-062).
gingival fibroblast serum-free culture medium with platelet lysate (KOS+P):
DMEM 80% (INVITROGEN, ref. 41966-029);
KNOCKOUT™ SR 20% (INVITROGEN, ref. 10828-028)+ platelet lysate;
Human recombinant bFGF 1 ng/ml (INVITROGEN, ref. 13256-029);
Human recombinant Zn Insulin 0-50 µg/ml (MW 5734) (INVITROGEN, ref. R33750)
Non-essential amino acids 1% (INVITROGEN, ref. 11140-035);
β-mercaptoethanol 0.1 mM (INVITROGEN, ref. 31350-010).
Antibiotic-Antimicotic 1×(penicillin 100 units/ml, streptomycin 100 µg/ml, and amphotericin B 250 ng/ml) (INVITROGEN, ref. 15240-062)

50,000 human gingival fibroblasts obtained as described in Gogly et al. (1999) *Biochem. Pharmacol.* 56:1447-1454 (see Example 1) are seeded per well of microculture plates (each well contains 1 ml of culture medium) each well further receiving either one of the above culture media (FCS, KOS and KOS+P). The cells are cultivated during six hours in the incubator at 37° C./5% $CO_2$ during which, each hour, the medium (FCS, KOS and KOS+P) from a set of wells was gently taken and the adherent cells are counted by flow cytometry after being recovered from the surface of the wells by trypsinization. A Trypan blue stain is shown on one well of each condition as a cell quality control.

Figure 5:
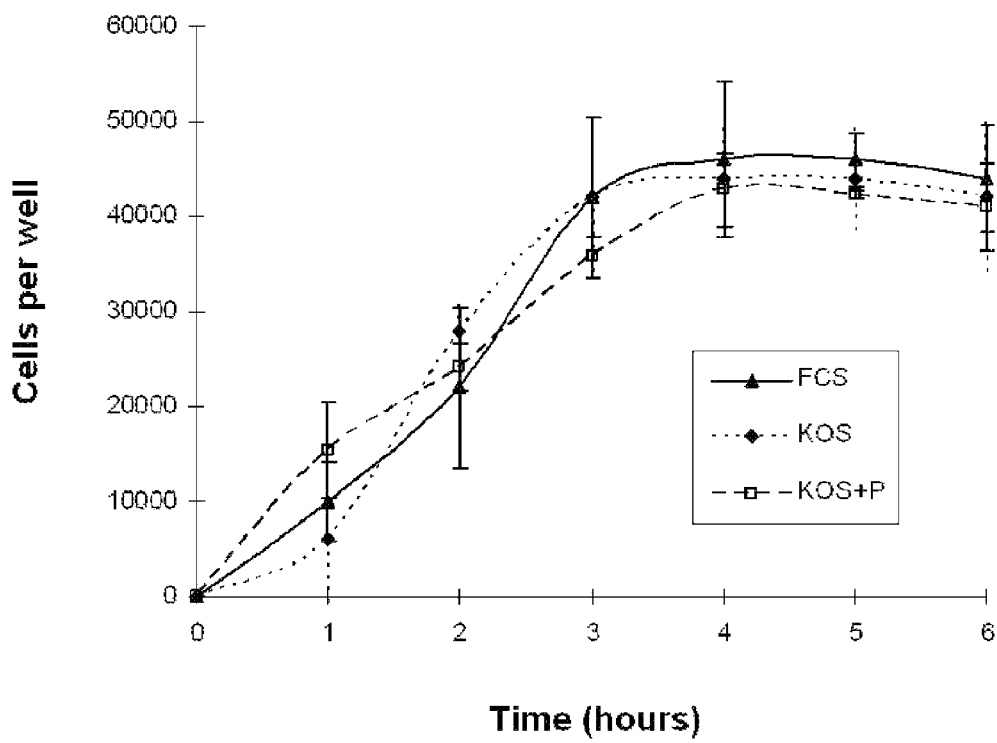
FIG. 5 represents gingival fibroblast adhesion (vertical axis, number of cells) as a function of time (horizontal axis, hours) in a culture medium containing 10% FCS (triangle shapes), in a culture medium free of animal serum supplemented with 1 ng/ml bFGF and 5 µg/ml insulin (KOS, diamond shapes), and in a culture medium free of animal serum supplemented with 1 ng/ml bFGF and 5 µg/ml insulin with platelet lysate (KOS+P, square shapes).

The results show that cells adhere to the surface of the wells from 3 to 4 hours after seeding, irrespective of the medium used (FIG. 5).

The experiments are repeated with the same media KOS and KOS+P as above, except for the DMEM/KNOCKOUT™ SR concentrations which are respectively of 90% and 10%.

Cellular counting shows no significant difference between the FCS medium and the serum-free medium with and without platelet lysate during the 6 hours following sowing. In all boxes, cell adhesion increases linearly to reach a level corresponding to about 80% of sown cells. Three hours are enough for most of the cells to adhere to the box bottom, however, in the presence of platelet lysate, 1 more hour is necessary to reach the 80% maximum.

Example 3

Proliferation Test 10,000 human gingival fibroblasts are seeded per 500 µl well of microculture plates, each well further receiving either one of the FCS, KOS and KOS+P culture media. The fibroblasts are then cultured over a 6-days period. Each day the media from a set of wells are gently taken and cells adhering to the walls of the wells are detached by trypsinization and counted by flow cytometry. A Trypan blue stain is shown on one well of each condition as a cell quality control.

Figure 6:
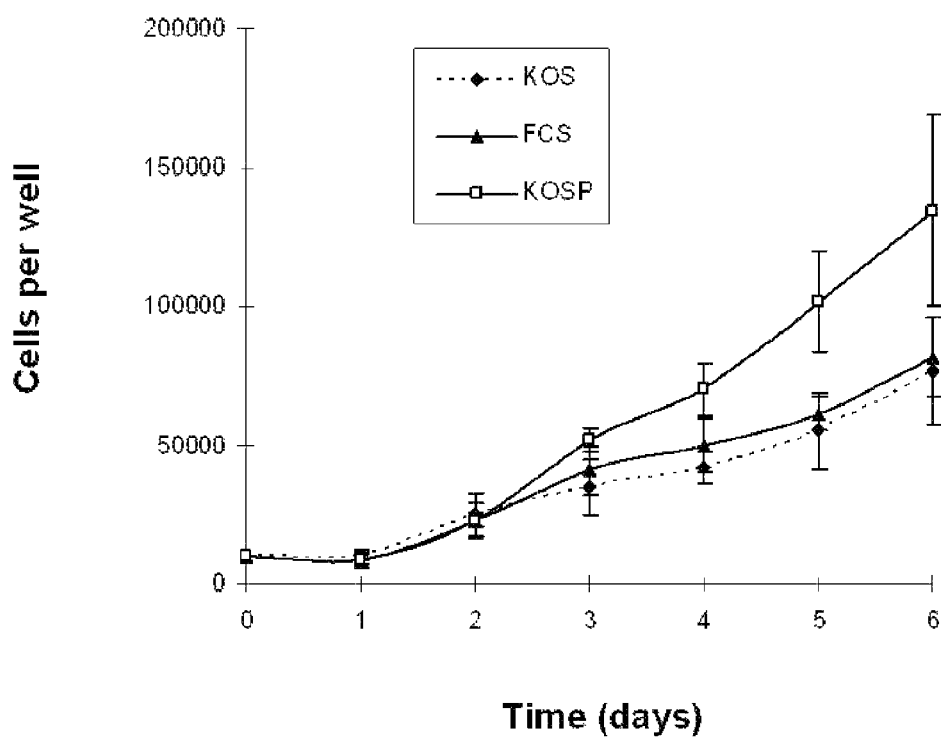
FIG. 6 represents gingival fibroblast growth (vertical axis, number of cells) as a function of time (horizontal axis, days) in a culture medium containing 10% FCS (triangle shapes), in a culture medium free of animal serum supplemented with 1 ng/ml bFGF and 5 µg/ml insulin (KOS, diamond shapes), and in a culture medium free of animal serum supplemented with 1 ng/ml bFGF and 5 µg/ml insulin with platelet lysate (KOS+P, square shapes).

The results are shown in FIG. 6. Growth with the KOS medium is similar to that obtained with the FCS medium. Addition of platelet lysate to the KOS medium significantly increases the growth of gingival fibroblasts.

These results are confirmed with the same KOS and KOS+P media as above, except for the DMEM/KNOCKOUT™ SR concentrations which are respectively of 90% and 10%. Briefly, the 6 days following sowing, cell quantity in the serum-free medium and in the FCS medium increases in a similar linear way, by a factor 10, whereas SF+PL increased significantly more (by a factor 17).

Example 4

Division Cycles 300,000 human gingival fibroblasts are seeded in culture flasks, each flask receiving one of the FCS, KOS or KOS+P medium. Each week during 6 weeks, media from one series of flasks are gently taken, and cells adhering to the walls of the wells are detached by trypsinization and counted. Flasks are then reseeded by 300,000 of the detached gingival fibroblasts. A Trypan blue stain is shown on one flask of each condition as a cell quality control.

Preliminary results indicate that gingival fibroblasts cultivated with the FCS and KOS media present from 2 to 2.5 divisions per week while the division rate is from 3 to 3.5 divisions per week with platelet lysate.

These results are confirmed with the same KOS and KOS+P media as above, except for the DMEM/KNOCKOUT™ SR concentrations which are respectively of 90% and 10%. Briefly, study during 6 weeks confirmed these increases and revealed a division weekly mean of 3 in BS and SF, compared with 3.8 for SF+PL. Standard deviations were more important in SF+PL cultures than in BS and SF.

Example 5

Culture Supernatant Analysis

In parallel to the study of Example 4 the culture medium of each flask is replaced by DMEM 24 hours prior to counting.

This medium is aliquoted and the following experiments are carried out to monitor parameters indicative of gingival fibroblast cellular activity and stress:

Zymogramms (MMP-1, MMP-2, MMP-3, MMP-9);
Western and dot blots (MMP-1, MMP-2, MMP-3, MMP-9, TIMP-1, TIMP-2);
ELISA (IL-1b, IL-4, IL-6, FGF, TGF-β1, TNF-α, etc);
RTPCR.

More specifically, for dot blotting, aliquots of conditioned media (100 μl) are centrifuged at 10,000 g to remove cellular debris and mixed with 10 μl of 1M Tris/HCl, 150 mM NaCl, pH 7.5. Samples (10 μl) are applied onto nitrocellulose membrane (Biorad). Membranes are treated with 1% blocking solution (Dako) for 1 h at room temperature. The membranes are then treated with primary mouse monoclonal antibodies of anti-human MMP-1, MMP2, MMP-3, MMP-7, MMP-9 freeforms (active and proforms) and anti-TIMP-1 and TIMP-2 (R&D system), at a dilution of 1/500, overnight at room temperature. Following washing in TBS/Tween (50 mM Tris, 150 mM NaCl, 0.1% Tween 20, pH 7.5), membranes are incubated with a peroxydase-labelled goat anti-mouse secondary antibody (1/1000, Calbiochem) for 1 hr and immunoreactive proteins visualized on Kodak Biomax MR film. Multiple exposures are examined to ascertain that the results analyzed reflect those produced in the linear range of the film. The size of the blot (surface area) and the intensity of the gray are analyzed using the Image J software (Image J; http:/rsb.info.nih.gov/ij/index.html). Concentration is determined by comparison with 10 pg MMP-1, MMP-2, MMP-3, MMP-7, MMP-9, TIMP-1 or TIMP-2 standards (R&D Systems). Statistical analysis between the different experiments is made using paired Student's t-test. Differences between groups are considered significant when p<0.01.

For zymography, conditioned culture medium samples (20 μl) are diluted by an equal volume of 1M Tris pH 6.8 containing 50% glycerol and 0.4% bromophenol blue, and then are electrophoresed in 10% SDS-polyacrylamide gels containing 1.5 mg/ml of gelatin for MMP-2 and MMP-9 revelations. Briefly, gels are washed in 2.5% Triton X-100, and incubated in 100 mM Tris-HCl, 5 mM $CaCl_2$, 0.005% Brij-35, and 0.001% $NaN_3$ pH 7.4 for 36 hr at 37° C. Gels are then stained with 0.25% Coomassie brilliant blue R-250 (50% methanol, 10% acetic acid) and destained appropriately (40% methanol, 10% acetic acid). Gelatinolytic activities correspond to the destained areas. 20 μl of MMP-2 and MMP-9 (ABCys) were electrophoresed at the same time to facilitate the MMP types identification.

Preliminary results do not show significant differences between gingival fibroblasts cultured in FCS and KOS media respectively.

These results are confirmed with the same KOS and KOS+P media as above, except for the DMEM/KNOCK-OUT™ SR concentrations which are respectively of 90% and 10%.

Briefly, dot blots detected free-forms of MMP-1, MMP-2, MMP-3, MMP-7 free-forms, TIMP-1 and TIMP-2. MMP-9 levels were under detection point. When referring to $10^5$ cells and compared to FCS, nearly equivalent MMPs and TIMPs levels are found in the FCS medium and in the serum-free medium (with and without platelet lysate) (see Table below).

| MMPs | | Weeks | | | | | |
|---|---|---|---|---|---|---|---|
| | | 1 | 2 | 3 | 4 | 5 | 6 |
| MMP-1 | FCS | 175 ± 16 | 213 ± 48 | 217 ± 51 | 224 ± 38 | 247 ± 45 | 348 ± 23 |
| | KOS | 254 ± 6 | 303 ± 57 | 335 ± 98 | 281 ± 5 | 299 ± 73 | 369 ± 76 |
| | KOS + P | 317 ± 49 | 236 ± 9 | 290 ± 27 | 231 ± 27 | 241 ± 11 | 251 ± 11 |
| MMP-2 | FCS | 208 ± 30 | 313 ± 24 | 198 ± 20 | 199 ± 34 | 190 ± 51 | 315 ± 32 |
| | KOS | 249 ± 28 | 264 ± 30 | 342 ± 33 | 216 ± 23 | 213 ± 22 | 300 ± 25 |
| | KOS + P | 248 ± 60 | 259 ± 48 | 318 ± 19 | 287 ± 12 | 299 ± 47 | 334 ± 29 |
| MMP-3 | FCS | 205 ± 10 | 189 ± 24 | 219 ± 14 | 221 ± 30 | 226 ± 12 | 354 ± 20 |
| | KOS | 274 ± 21 | 352 ± 39 | 315 ± 41 | 201 ± 15 | 236 ± 32 | 274 ± 33 |
| | KOS + P | 334 ± 37 | 244 ± 38 | 307 ± 34 | 190 ± 34 | 190 ± 21 | 240 ± 41 |
| MMP-7 | FCS | 361 ± 24 | 276 ± 11 | 229 ± 15 | 290 ± 26 | 146 ± 16 | 120 ± 20 |
| | KOS | 308 ± 11 | 278 ± 12 | 302 ± 24 | 226 ± 12 | 300 ± 36 | 290 ± 28 |
| | KOS + P | 244 ± 16 | 235 ± 12 | 259 ± 13 | 237 ± 61 | 212 ± 28 | 186 ± 25 |
| TIMP-1 | FCS | 216 ± 24 | 304 ± 12 | 215 ± 16 | 260 ± 28 | 240 ± 12 | 298 ± 26 |
| | KOS | 208 ± 15 | 299 ± 23 | 308 ± 24 | 263 ± 44 | 209 ± 41 | 267 ± 40 |
| | KOS + P | 179 ± 12 | 244 ± 18 | 201 ± 39 | 173 ± 54 | 195 ± 41 | 169 ± 36 |
| TIMP-2 | FCS | 207 ± 27 | 233 ± 19 | 263 ± 15 | 226 ± 27 | 212 ± 25 | 230 ± 29 |
| | KOS | 184 ± 12 | 219 ± 26 | 212 ± 10 | 179 ± 12 | 179 ± 23 | 189 ± 14 |
| | KOS + P | 119 ± 20 | 129 ± 12 | 162 ± 25 | 170 ± 35 | 124 ± 14 | 118 ± 22 |

Gelatin zymography confirmed the MMP-9 absence observed on dot blots since MMP-9 activity could not be detected on gelatin zymography.

Example 6

Cytoskeleton Proteins

Gingival fibroblasts are cultured for one week in the FCS or KOS medium using the lab teck technique described in Prost et al. (1998) *FASEB* 12:181-188 in order to study cytoskeleton proteins (e.g. actine, vimentine, desmine) in the frame of the monitoring of modifications of the cytoskeleton indicative of transformation of the gingival fibroblasts into myofibroblasts (i.e. enrichment in actin).

Briefly, at each passage, about $10^2$ gingival fibroblasts (from proliferation study) are cultured on Lab-Tek chamber slides with cover (Nalge Nunc International, USA) Before becoming confluent, gingival fibroblast are fixed with a 4% paraformaldehyde solution for 15 min at 4° C., and washed three times with PBS. They are then incubated for 1 h with a 1:50 dilution of anti-actin, and anti-vimentin (BD PharMingen, USA) and a dilution of 1:100 of anti-desmin (BD PharMingen, USA). After being thoroughly washed with PBS, cells are incubated for 30 min at 37° C. with a rhodamine-labeled goat anti-mouse secondary antibody (R&D Systems, USA) diluted 1:100 with PBS. The dishes are washed three times with PBS, and the chambers are removed from the slides. Cells are examined with a microscope (Leica, Germany) equipped with epifluorescence (ebq100, Leica) and with filters for rhodamine fluorescence. Fluorescence is recorded on a computer by a Leica DC300F camera.

Preliminary results do not show significant differences between gingival fibroblasts cultured in FCS and KOS media respectively.

This is confirmed for the same KOS and KOS+P media as above, except for the DMEM/KNOCKOUT™ SR concentrations which are respectively of 90% and 10%. Briefly, gingival fibroblasts express vimentin constantly and similarly in all the media tested. The percentage of α-SM-actin positive cells increases significantly with the number of passages. Almost all cells are lightly positive for actin at week 6. Cells are negative for desmin.

Example 7

Form Factors

Each week human gingival fibroblasts in long term flask cultures in the FCS, KOS, or KOS+P medium are photographed to monitor changes in the surface (S) and perimeter (P) of the cells. The form factor (FF) of the cells is then determined using the following formula: $FF=4\pi(S/P^2)$.

Figure 7:
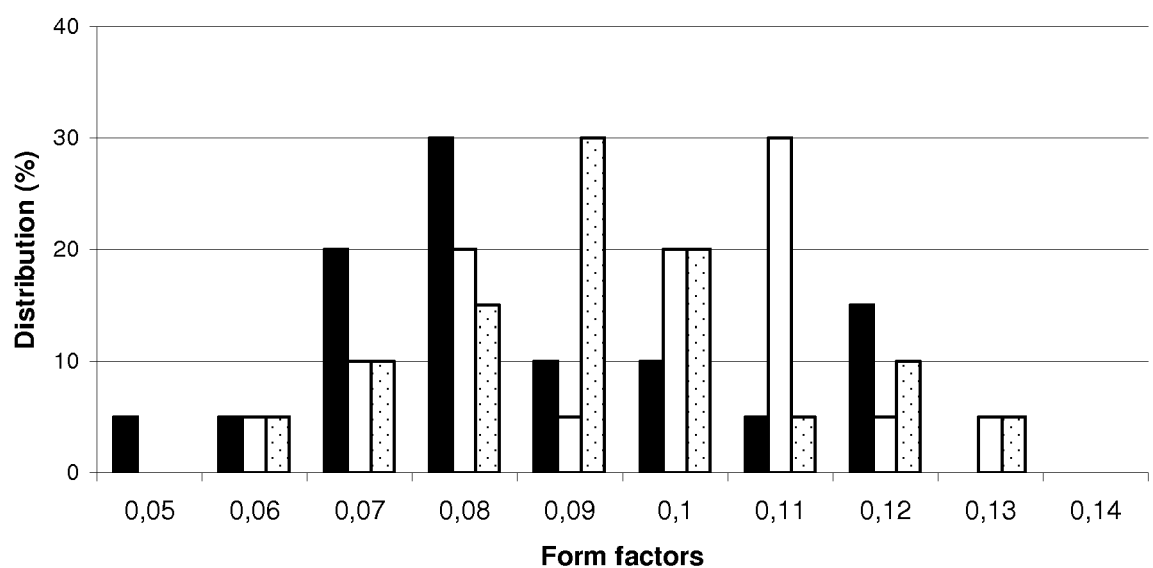
FIG. 7 represents the distribution (vertical axis, in %) of fibroblast gingival form factors at week 7 of culture in a culture medium containing 10% FCS (white bars), in a culture medium free of animal serum supplemented with 1 ng/ml bFGF and 5 µg/ml insulin (KOS, black bars), and in a culture medium free of animal serum supplemented with 1 ng/ml bFGF and 5 µg/ml insulin with platelet lysate (KOS+P, dotted bars).

The results are presented in FIG. 7. No significant differences between gingival fibroblasts cultured in FCS, KOS and KOS+P media can be evidenced, with the form factors varying from 0.05 to 0.13, which corresponds to classical gingival fibroblasts (Serra J. *Image analysis and mathematical morphology* London. Academic press, Vol 1, 1982. Vol 2, 1988).

All afore-cited publications are incorporated herein by reference.

The invention claimed is:

1. A method for the culture of gingival fibroblasts which comprises growing gingival fibroblasts in a gingival fibroblast culture medium, wherein said medium comprises a culture medium for animal or human cells, free of animal serum to which is added: from 0.1 ng/ml to 100 ng/ml bFGF and from 1 µg/ml to 50 µg/ml insulin.

2. A kit for cultivating gingival fibroblasts, comprising:
    a gingival fibroblast culture medium comprising a culture medium for animal or human cells, free of animal serum to which is added: from 0.1 ng/ml to 100 ng/ml bFGF and from 1 µg/ml to 50 µg/ml insulin and
    platelet lysate.

3. The method according to claim 1, wherein bFGF is added at 1 ng/ml.

4. The method according to claim 1, wherein insulin is added at 5 μg/ml.

5. The method according to claim 1, wherein the gingival fibroblast culture medium free of animal serum comprises bFGF at 1 ng/ml and insulin at 5 μg/ml.

6. The method according to claim 1, wherein the gingival fibroblast culture medium free of animal serum further comprises platelet lysate.

* * * * *